US00PP18559P2

(12) United States Plant Patent
Zaiger et al.

(10) Patent No.: US PP18,559 P2
(45) Date of Patent: Mar. 4, 2008

(54) **INTERSPECIFIC *PRUNUS* TREE NAMED 'CRIMSON ROYALE'**

(50) Latin Name: *Prunus*
Varietal Denomination: Crimson Royale

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 18 days.

(21) Appl. No.: 11/526,261

(22) Filed: Sep. 25, 2006

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

PP12,097 P2 * 9/2001 Zaiger et al. ..... Plt./180

* cited by examiner

*Primary Examiner*—Wendy Haas

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with excellent flavor and eating quality.
2. Heavy and regular production of fruit.
3. Fruit with an attractive red skin color.
4. Fruit with a high average Brix of 22.8° and a good balance between acid and sugar.
5. Fruit hanging firm on the tree approximately 2 weeks after maturity.
6. Tree with vigorous, upright growth.

1 Drawing Sheet

Botanical classification: *Prunus* species.

BACKGROUND OF THE VARIETY

FIELD OF INVENTION

In the field of plant genetics, we conduct an extensive and continuing plant-breeding program including the organization and asexual reproduction of orchard trees, and of which plums, peaches, nectarines, apricots, cherries and interspecifies are exemplary. It was against this background of our activities that the present variety of interspecific tree was originated and asexually reproduced by us in our experimental orchard located near Modesto, Stanislaus County, Calif.

PRIOR VARIETIES

The existing variety of interspecific tree, which is known to us, and mentioned herein, 'Flavor Grenade' Interspecific (U.S. Plant Pat. No. 12,097).

ORIGIN OF THE VARIETY

The new and distinct variety of interspecific tree, multiples of [*Prunus salicina*×(*Prunus salicina*×(*Prunus salicina*×*Prunus armeniaca*)], was developed by us in our experimental orchard located near Modesto, Calif., from seed of an open pollinated 'Flavor Grenade' Interspecific (U.S. Plant Pat. No. 12,097), (the pollen parent is unknown). In 1997 we budded a large number of these open pollinated seedlings to established trees of 'Nemaguard' Rootstock (non-patented), to enhance early production of fruit. Under close and careful observation the present variety exhibited desirable tree and fruit characteristics and was selected in 1999 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree [Plum×(Plum×Plumcot)] is of large size, vigorous, upright growth, and a productive and regular bearer of large size, yellow fleshed, clingstone fruit with an attractive red skin color. The fruit is further characterized by having a good balance between acid and sugar, excellent flavor and eating quality with an average Brix of 22.8°. The size of fruit is relatively uniform throughout the tree and holds firm approximately 14 days after maturity (shipping ripe). In comparison to its maternal parent 'Flavor Grende' Interspecific (U.S. Plant Pat. No. 12,097), the fruit of the new variety is larger in size, has more attractive red skin color and is approximately 5 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree 6 years of age, its flowers, foliage and fruit, as based on observations of 6 year old specimens grown near Modesto, Calif., with color in accordance with Munsell Book of Color.

Tree:

*Size.*—Large, pruned to 3 to 3.5 meters in height for economical harvesting of fruit. Average spread 3 meters, varies with different cultural practices.

*Vigor.*—Vigorous, tree growth of approximately 1.5 to 2 meters in height the first growing season.

*Form.*—Upright, usually pruned to vase shape.

*Branching habit.*—Upright, crotch angle approximately 35°, increases with heavy crop load.

*Productivity.*—Productive. Thinning and spacing of fruit necessary for desired market size.

*Bearer.*—Regular, adequate fruit set 4 consecutive years, no alternate bearing observed.

*Fertility.*—Self sterile, pollinator required.

*Density.*—Medium dense, usually pruned to vase shape to allow more sunlight to center of tree to enhance fruit color and health of fruit spurs.

*Hardiness.*—Hardy in all some fruit growing areas of California. Grown in USDA Hardiness Zone 9. Winter chilling requirement approximately 550 hours at or below 45° F.

Trunk:

*Size.*—Medium to large. Average circumference 48.3 cm measured at 25.4 cm above ground level on 6 year old trees.

*Texture.*—Medium shaggy, increases with age of tree.

*Color.*—Varies from 10YR 5/2 to 2.5Y 3/2.

Branches:

*Size.*—Medium. Average circumference 14.3 cm at 1 meter above ground.

*Surface texture.*—New growth relatively smooth, mature growth medium rough, roughness increases with age.

*Lenticels.*—Average number 29 in a 25.8 square cm surface of branch. Average length 3.5 mm. Average width 1.3 cm. Color varies from 5YR 5/8 to 7.5YR 5/8.

*Color.*—New growth varies from 5GY 5/6 to 10YR 4/6. Old growth varies from 7.5YR 6/2 to 7.5YR 3/2, varies with age of growth.

Leaves:

*Size.*—Medium to large. Average length 113.4 mm. Average width 45.9 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentation over midrib and leaf veins, glabrous. Lower surface relatively smooth, except for small ridges created by midrib and pinnate venation, glabrous.

*Petiole.*—Size — medium. Average length 17.3 mm. Average width 1.5 mm. Color varies from 10Y 8/6 to 2.5GY 7/6. Longitudinally grooved, glabrous.

*Glands.*—Type — globose. Size — small. Average length 1.0 mm. Average diameter 0.5 mm. Average number 2, varies from 1 to 3. Located primarily on base of leaf blade and upper portion of petiole. Color varies from 2.5GY 6/6 to 2.5GY 5/6.

*Color.*—Upper surface varies from 5GY 3/4 to 5GY 3/6. Lower surface varies from 5GY 4/4 to 7.5GY 4/4. Midvein color varies from 2.5GY 8/6 to 2.5GY 7/6.

Flower buds:

*Size.*—Medium. Average length 11.3 mm. Average width 6.1 mm.

*Hardiness.*—Hardy in all stone fruit growing areas of California.

*Form.*—Conical, becomes slightly elongated just before opening.

*Pedicel.*—Surface — glabrous. Average length 10.5 mm. Average width 0.6 mm. Color varies from 2.5GY 7/6 to 2.5GY 6/8.

*Color.*—N 9.5/ (white).

*Number of buds per spur.*—Average 5, varies from 4 to 7 varies with age of spur.

Flowers:

*Size.*—Medium. Average height 12.4 mm. Average diameter 23.1 mm.

*Petals.*—Number — 5, alternately arranged to sepals. Form — obovate, narrows at point of attachment. Size — medium. Average length 11.8 mm. Average width 9.0 mm. Margin — sinuate. Both surfaces glabrous. Color — N 9.5/ (white).

*Sepals.*—Number — 5, alternately arranged to petals. Shape — triangular, apex rounded. Margin — entire. Size — small to medium. Average length 3.3 mm. Average width 3.1 mm. Both surfaces glabrous. Color — upper surface varies from 2.5GY 6/8 to 5GY 6/8. Lower surface varies from 5GY 6/8 to 5GY 5/6.

*Stamens.*—Average number 31. Average filament length 9.9 mm. Filament color N 9.5/ (white). Anther color varies from 5Y 8/10 to 5Y 7/10.

*Pollen.*—Self sterile, pollinator required. Color varies from 5Y 7/10 to 5Y 7/12.

*Pistil.*—Usually 1, varies from 1 to 2. Average length 11.7 mm. Position of stigma approximately same height as anthers. Color varies from 2.5GY 8/4 to 2.5GY 4/6. Surface — glabrous.

*Fragrance.*—Slight aroma.

*Blooming period.*—Date of First Bloom Feb. 18, 2005. Date of Petal Fall Mar. 1, 2005, varies slightly with climatic conditions.

*Color.*—N 9.5/ (white).

*Number flowers per flower bud.*—Average 2, varies from 1 to 3.

*Pedicel.*—Average length 12.6 mm. Average width 0.7 mm. Color varies from 2.5GY 7/8 to 2.5GY 6/6.

Fruit:

*Maturity when described.*—Firm ripe.

*Date of first picking.*—Jul. 29, 2005.

*Date of last picking.*—Aug. 7, 2005, varies slightly with climatic conditions.

*Size.*—Large. Average diameter axially 72.7 mm. Average transversely is suture plane 63.1 mm. Average weight 184.6 grams, varies with fertility of the soil, amount of thinning and climatic conditions.

*Form.*—Elongated.

*Suture.*—Shallow, extends from base to apex.

*Ventral surface.*—Slightly lipped, some fruit more than others.

*Apex.*—Rounded to slightly pointed.

*Base.*—Retuse.

*Cavity.*—Rounded to slightly elongated in suture plane. Average depth 4.0 mm. Average diameter 11.3 mm.

Stem:

*Size.*—Large. Average length 22.2 mm. Average diameter 1.6 mm.

*Color.*—Varies from 10Y 6/6 to 7.5YR 5/6.

Flesh:

*Ripens.*—Evenly.

*Texture.*—Firm, meaty.

*Fibers.*—Few, small, tender.

*Firmness.*—Good, comparable to other commercial interspecific varieties.

*Aroma.*—Slight.

*Amydgalin.*—Undetected.

*Eating quality.*—Excellent.

*Flavor.*—Excellent, good balance between acid and sugar.

*Juice.*—Heavy, enhances flavor.

*Brix.*—Average 22.8°, varies slightly with amout of fruit per tree and climatic conditions.

*Color.*—Varies from 5Y 9/6 to 7.5Y 9/4. Pit cavity varies from 2.5Y 7/6 to 2.5Y 6/6.

Skin:

*Thickness.*—Medium.

*Surface.*—Relatively smooth, very slightly waffled.

*Bloom.*—Moderate amount, complete coverage.

*Tendency to crack.*—None.

*Color.*—Ground color varies from 2.5Y 9/4 to 2.5Y 8.5/8. Overspread with 5R 3/8 to 7.5R 2/8. Very small, randomly spaced areas of ground color exposed giving a speckling pattern to skin.

*Tenacity.*—Tenacious to flesh.

Stone:

*Type.*—Clingstone.

*Size.*—Large. Average length 29.6 mm. Average width 19.9 mm. Average thickness 10.7 mm.

*Form.*—Obovoid.

*Base.*—Varies from flat to concaved.

*Apex.*—Rounded.

*Surface.*—Slightly pitted throughout, one long groove on each side of suture, extending from base to apex.

*Sides.*—Unequal, with one side extending further from suture plane.

*Ridges.*—One small, long, narrow ridge on each side of suture, small, short ridges extending from base toward apex.

*Tendency to split.*—None.

*Color.*—Varies from 7.5YR 6/6 to 7.5YR 5/8 when dry.

Kernel:

*Form.*—Ovate.

*Taste.*—Bitter.

*Viability.*—Viable, embryo fully developed.

*Size.*—Medium. Average length 15.6 mm. Average width 9.9 mm. Average depth 6.0 mm.

*Skin.*—Color varies from 2.5Y 8.5/4 to 5Y 9/4 when dry.

Use: Dessert.

*Market.*—Local and long distance.

Keeping quality: Good, held firm in cold storage for 21 days at 38° to 42° F. without internal breakdown of flesh or appreciable loss of flavor.

Shipping Quality: Good, minimal flesh bruising or skin scarring during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth, heavy production, regular bearing of large, attractive red skin fruit with excellent flavor and eating quality; the fruit is further characterized by having firm flesh, holding first on the tree approximately 14 days after maturity (shipping ripe), with good handling and shipping quality.

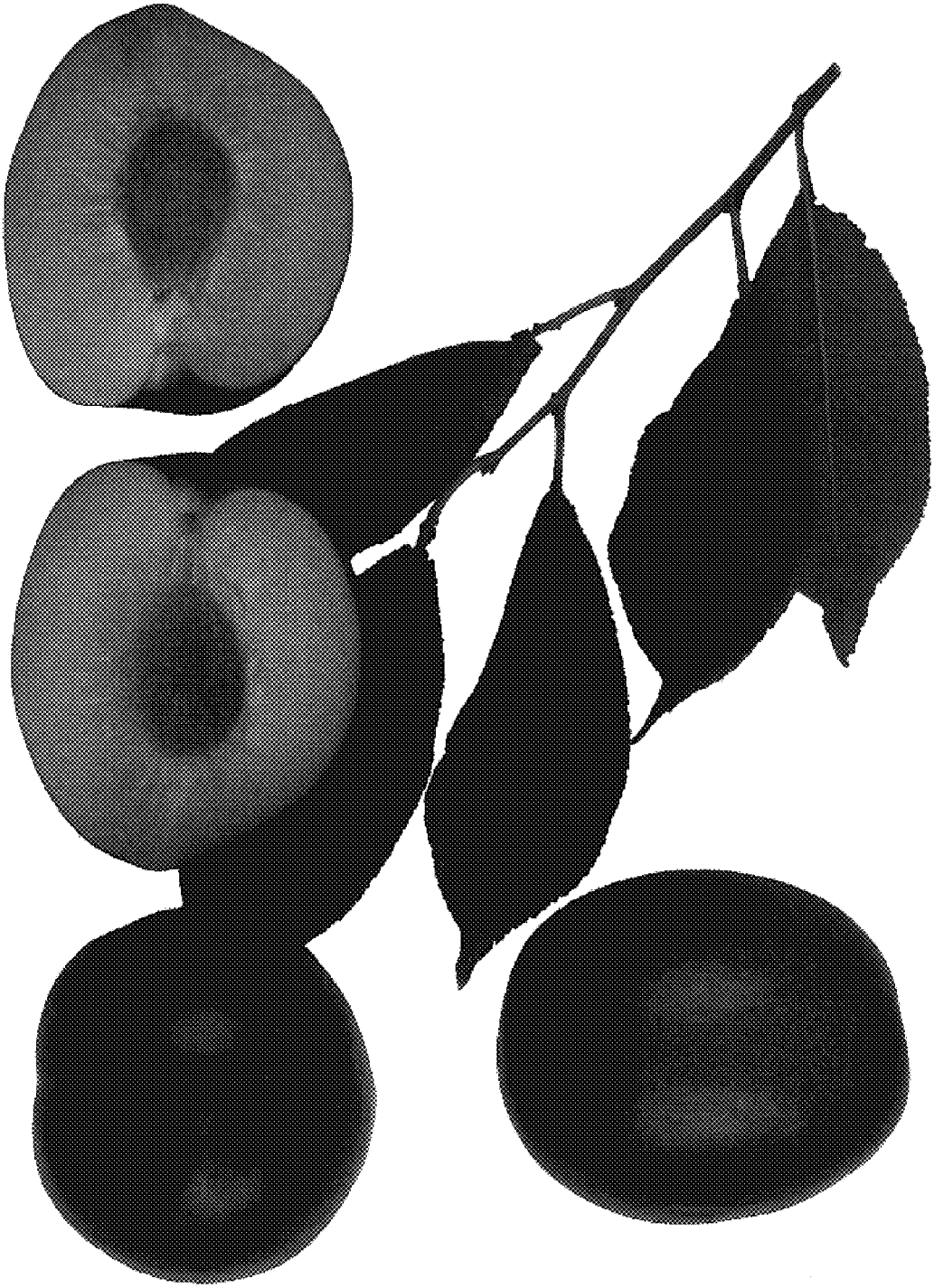

* * * * *